US006310272B1

(12) United States Patent
Ohashi et al.

(10) Patent No.: US 6,310,272 B1
(45) Date of Patent: Oct. 30, 2001

(54) STRESS RESISTANT PLANT IN WHICH CELL DEATH SUPPRESSING GENE IS INTRODUCED AND METHOD FOR PRODUCING THE SAME

(75) Inventors: Yuko Ohashi; Ichiro Mitsuhara; Kamal A. Malik, all of Tsukuba (JP)

(73) Assignee: Director General of National Institute of Agrobiological Resources, Ministry of Agriculture, Forestry and Fisheries, Ibaraki (JP)

(*) Notice: Subject to any disclaimer, the term of this patent is extended or adjusted under 35 U.S.C. 154(b) by 0 days.

(21) Appl. No.: 09/037,746

(22) Filed: Mar. 10, 1998

(30) Foreign Application Priority Data

Mar. 11, 1997 (JP) .................................... 9-956743
Jan. 19, 1998 (JP) .................................... 10-108056

(51) Int. Cl.[7] .............................. C12N 15/82; C12N 5/04; A01H 5/00; A01H 5/10; A01H 4/00
(52) U.S. Cl. ......................... 800/278; 800/288; 800/298; 800/301; 435/468; 435/410; 435/419; 435/418
(58) Field of Search ..................................... 800/278, 288, 800/298, 301; 435/468, 410, 419, 418

(56) References Cited

FOREIGN PATENT DOCUMENTS

| WO 98/04586 | 2/1998 | (WO) | .......................... C07K/14/415 |
|---|---|---|---|
| WO 98/37755 | 9/1998 | (WO) | .............................. A01H/5/00 |
| WO 98/39422 | 9/1998 | (WO) | .............................. C12N/9/02 |
| WO 98/46775 | 10/1998 | (WO) | .......................... C12N/15/82 |
| WO 98/54961 | 12/1998 | (WO) . | |

OTHER PUBLICATIONS

Napoli et al. The Plant Cell. 1989. vol. 2: 278–289.*
Carvalho et al. The EMBO J. 1992. 2595–2602.*
Tepperman et al. Plant Molecular Biology. 1990. vol. 14: 501–511.*
Gupta et al. Proc. Natl. Acad. Sci. 1993. vol. 15: 1629–1633.*
Korsmeyer et al. Cancer Surv. 1992. vol. 15: 105–118.*
Dole et al. Cancer Res. 1995. vol. 55: 2576–2582.*
Hengartner et al. Cell. 1994. vol. 76: 665–676.*
Mittler, et. al.: "Inhibition of Programmed Cell Death in Tobacco Plants during a Pathogen–Induced Hypersensitive Response at Low Oxygen Pressure" *The Plant Cell*, 11/96; vol. 8, pp. (1991–2001).
Randy D. Allen: "Dissection of Oxidative Stress Tolerance Using Transgenic Plants" *Plant Physiology* (1995) vol. 107, (pp. 1049–1054).

Tarczynski, et. al.: "Stress Protection of Transgenic Tobacco by Production of the Osmolyte Mannitol" *Science*; Jan. 22, 1993; vol. 259 pp. (508–510).
Deping Xu, et. al.: "Expression of a Late Embryogenesis Abundant Protein Gene, HVA1, from Barley Confers Tolerance to Water Deficit and Salt Stress in Transgenic Rice[1]" *Plant Physiology*, (1996), vol. 110(1) pp. (247–257).
Dietrich, et. al.: "A Novel Zinc Finger Protein Is Encoded by the Arabidopsis LSD1 Gene and Functions as a Negative Regulator of Plant Cell Death", *Cell*, Mar. 7, 1997; pp. (685–694).
Malik, et. al.: "Bcl–xL and ced–9 confer resistance to Uv and paraquat in transgenic tobacco plant" *Plant Physiology Supplement, Poster Annual Meeting of American Society of Plant Physiologists*; 7/97; vol. 114(3), p. 295 Abstract.
Johal, et. al.: "Disease lesion mimics of maize: A model for cell death in plants" *BioEssays* Jan. 1, 1995; vol. 17(8) pp. (685–692).
M. Miura, *Cell Technology*, vol. 14, No. 2, pp. 145–153, 1995 with partial English translation.
Y. Eguchi et al., *Experimental Medicine*, vol. 13, No. 16, pp. 1828–1833, 1995 with partial English translation.
S. Takayama, *Experimental Medicine*, vol. 13, No. 16, pp. 1834–1841, 1995 with partial English translation.
T. Yamamoto, *Experimental Medicine, Supp.*, pp. 138–139, 1996 with partial English translation.
H. Fukuda, *Kagaku to Seibutsu*, vol. 34, No. 9, pp. 586–594, 1996 with partial English translation.
S. Ohta et al., *Experimental Medicine*, vol. 13, No. 16, pp. 1842–1847, 1995 with partial English translation.
S. Kumar et al., *Genes & Development*, 8, pp. 1613–1626, 1994.
D.E. Sleat et al., *Gene*, 217, pp. 217–225, 1987.
M. Oshima et al., Japanese Laid–Open Publication No. 7–250685, Laid open on Oct. 3, 1995 with partial English translation.
R. Nagel et al., , *FEMS Microbiology Letters*, 67, pp. 325–328, 1990.
H. Ito et al., *Plant Cell Reports*, 13, pp. 361–366, 1994.
R.J. Porra et al., *Biochimica et Biophysica Acta*, 975, pp. 384–394, 1989.

* cited by examiner

*Primary Examiner*—Lynette R. F. Smith
*Assistant Examiner*—Ousawa M-Faiz Zaghmout
(74) *Attorney, Agent, or Firm*—Townsend and Townsend and Crew LLP

(57) ABSTRACT

The present invention provides a stress resistant plant in which a cell death suppressing gene is introduced.

8 Claims, 14 Drawing Sheets

(8 of 14 Drawing Sheet(s) Filed in Color)

M66 PLANT

STRESS RESISTANT PLANT IN WHICH CELL DEATH SUPPRESSING GENE IS INTRODUCED AND METHOD FOR PRODUCING THE SAME

BACKGROUND OF THE INVENTION

1. Field of the Invention

The present invention relates to a stress resistant plant and a method for producing the stress resistant plant. More specifically, the present invention relates to the breeding of a stress resistant plant by introducing a cell death suppressing gene into a plant.

2. Description of the Related Art

Today, research on programmed cell death (hereinafter, simply referred to as "PCD") of multicellular organisms has become enthusiastic. PCD is appreciated as essential to ontogenesis, homeostasis, resistance to environmental stresses, or the like of an organism. Research on PCD is mainly performed on *Caenorhabditis elegans* (hereinafter, simply referred to as "*C. elegans*"), drosophila and mammals (e.g., Miura et al., *Cell Technology*, vol. 14, No. 2:145–153, 1995). For example, research on *C. elegans* revealed some cell death genes (e.g., ced-3 and ced-4) and some cell death suppressing genes (e.g., ced-9). The cell death suppressing genes are considered to negatively regulate activities of the cell death genes, thereby suppressing random cell death.

A protein encoded by a bcl-2 gene found in mammals (i.e., a Bcl-2 protein) exhibits a cell death suppressing activity in cells of various systems (i.e., cells of lymphoid system, nervous system, reproductive system and epithelial system). So far, cell death which may be induced by various processes is known to be suppressed by overexpression of Bcl-2 (e.g., Eguchi et al., *Experimental Medicine*, vol. 13, No. 16, 18–23, 1995).

Recently, many genes encoding for Bcl-2 related protein and Bcl-2 binding protein are reported. These genes are classified into a Bcl-2 family. Examples of genes belonging to the Bcl-2 family include bcl-2, bax, bcl-xL, bcl-xS, bad, bak, A1 and Mcl-1 genes derived from mammals, a ced-9 gene derived from *C. elegans,* and a BHRF1 gene (derived from Epstein-Barr virus) and a LMW5-HL gene (derived from African Swine Fever virus) (Takayama, *Experimental Medicine*, vol. 13, No. 16, 24–31, 1995). Generally, it is known in the art that identity and similarity among the genes belonging to the Bcl-2 family are very low at a nucleic acid sequence level and also at an amino acid sequence level. For example, identity between Baxα and Bcl-2 is about 21% and similarity therebetween is about 43% at their amino acid sequence level (Yamamoto, "Intercellular Signal Transduction", *Experimental Medicine, supp.*, Adduce Co., Ltd.).

Study on PCD of higher plants has just begun recently (see Fukuda et al., *Kagaku TO Seibutsu,* 34:586–594, 1996). Plants are always exposed to severe stresses. For example, a plant may be infected with virus or bacteria, may be irradiated with UV light, or may be affected by peroxide caused by herbicide. In order to withstand these stresses, for example, in the case of a virus infection, a hypersensitive response (HR) induces PCD. The HR is characterized by the rapid appearance of necrotic lesion at the site of the infection. Although the HR involves some tissue damage, its results is to protect the plant by limiting the spread of the infection. Again, such PCD in a plant is considered to involve the cell death gene and the cell death suppressing gene.

Seeing that a cell death suppressing gene is presumably capable of negatively regulating cell death resulting from stress (i.e., capable of preventing cell death) or the like, the cell death suppressing gene is considered to have resistance against stresses. Accordingly, in breeding a plant, the plant may be conferred resistance to stresses by expressing a cell death suppressing gene. Providing a plant which is conferred resistance to environmental stresses is a vital subject in the field of agriculture. Today, the amount of UV (UV-B) light that we are actually receiving is increased by about 6.8% per decade due to destruction of the ozone layer, and the like. Apparently, plants, are also confronting this environmental problem.

However, at present, to the extent that the inventors are aware of, prior to the filing of Japanese Patent Applications Nos. 9-56743 and 10-8056 on which the present application claims priority, no study has been made to the use of a cell death suppressing gene for acquiring resistance to environmental stresses such as UV light, a herbicide which generates superoxide and salt stress.

SUMMARY OF THE INVENTION

The present invention relates to a stress resistant plant in which a cell death suppressing gene is introduced. The cell death suppressing gene is introduced into DNA of plant cells by a known gene recombinant technique. The DNA of the plant cells refer to not only chromosomal DNA but also to DNA of various organelles (e.g., mitochondria, chloroplast, etc.) in the plant cells.

According to one aspect of the present invention, a stress resistant plant is provided in which a cell death suppressing gene is introduced.

In one embodiment of the present invention, the cell death suppressing gene belongs to a Bcl-2 family and encodes for a peptide having a cell death suppressing activity.

In one embodiment of the present invention, the cell death suppressing gene is a *Caenorhabditis elegans* ced-9 gene.

In one embodiment of the present invention, the cell death suppressing gene is a human bcl-xL gene.

In one embodiment of the present invention, the stress is a stress caused by UV irradiation.

In one embodiment of the present invention, the stress is a oxidative stress caused by a herbicide which generates superoxide.

In one embodiment of the present invention, the stress is a stress caused by salt.

According to another aspect of the present invention, a method for producing a stress resistant plant includes the steps of: introducing a cell death suppressing gene into a plant cell; and regenerating the plant cell in which the cell death suppressing gene is introduced into a plant body.

In one embodiment of the present invention, the cell death suppressing gene is incorporated into a plant expression vector.

Thus, the invention described herein makes possible the advantages of (1) providing a plant which is conferred resistance to various stresses by introducing a gene relating to PCD into the plant; and (2) providing a method for breeding a plant which is conferred resistance to various stresses, where a gene relating to PCD is introduced into the plant.

These and other advantages of the present invention will become apparent to those skilled in the art upon reading and understanding the following detailed description with reference to the accompanying figures.

BRIEF DESCRIPTION OF THE DRAWINGS

The file of this patent contains four drawings executed in color. Copies of this patent with color drawings will be provided by the U.S. Patent and Trademark Office upon request and payment of the necessary fee.

DESCRIPTION OF THE PREFERRED EMBODIMENTS

Figure 1:
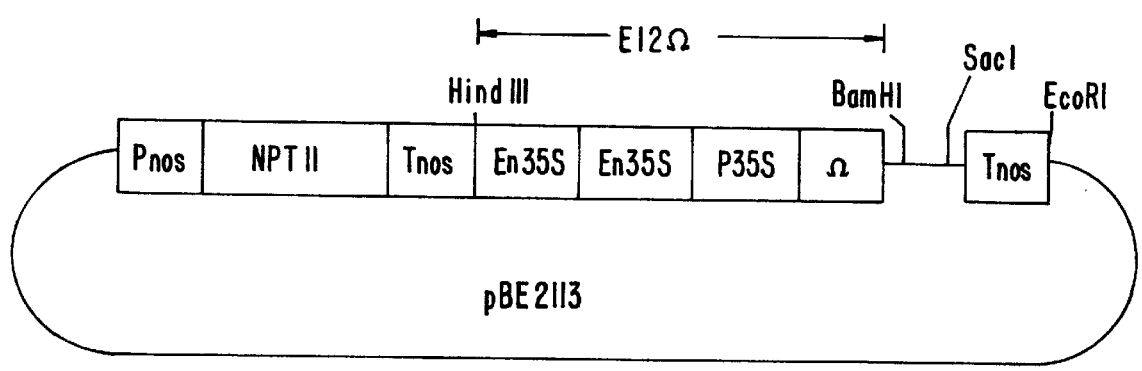
FIG. 1 is a schematic diagram showing a structure of the starting vector pBE2113.

Hereinafter, the present invention will be described in detail.

Herein, the term "cell death suppressing gene" refers to a gene which acts in a suppressive manner against PCD, regardless of origin (a plant or an animal) thereof as long as the gene is derived from a multicellular organism. The cell death suppressing gene is preferably one derived from an animal. For example, the cell death suppressing gene may be derived from nematodes (e.g., C. elegans) or mammals including human. Examples of the cell death suppressing gene include a ced-9 gene from C. elegans, a bcl-2 gene from mammals, for example, human, mouse or chicken, and a bcl-xL gene from human (Miura et al., *Cell Technology*, vol. 14, No. 2:145–153, 1995).

According to the present invention, a known cell death suppressing gene may be used. Preferable cell death suppressing genes include those belonging to the Bcl-2 family (e.g., the ced-9 gene and the bcl-xl gene).

Genes derived from genomic or cDNA libraries of various types of organisms, which may be obtained by using a known cell death suppressing gene or a fragment thereof as a probe, and which is homologous to the known cell death suppressing gene, may also be used as the cell death suppressing gene. For this purpose, for example, a plant DNA library, a C. elegans DNA library and a human DNA library may be used. Stringent conditions for screening the libraries may be suitably selected by those skilled in the art. Herein, "a gene having homology" refers to a gene which, when compared with a cell death suppressing gene at an amino acid level, is highly conserved in a particular region. The term "highly conserved" as used herein refers to, for example, having a homology at an amino acid level of about 40% or more, preferably about 70% or more, more preferably about 80% or more and still more preferably about 90% or more. In this context, the homology is determined as a ratio of the unchanged amino acids and the conservatively substituted amino acids based on the total amino acids compared between the two amino acids sequences.

Genes belonging to Bcl-2 family have highly conserved regions at an amino acid level. It has been known that BH1 and BH2 regions are highly conserved. It has also been known that there is a region at N-terminal side which is also highly conserved (i.e., a BH3 region). These regions are evolutionally conserved among heterogenous Bcl-2 families (human, mouse, rat and chicken) (Takayama, *Experimental Medicine*, vol. 13, No. 16, 24–31, 1995; and Ohta et al, *Experimental Medicine*, vol. 13, No. 16, 32–37, 1995). Especially a protein including all of the BH1, BH2 and BH3 regions is known to suppress apoptosis by itself (Takayama, *Experimental Medicine*, vol. 13, No. 16, 24–31, 1995).

Thus, the term "gene belonging to Bcl-2 family" refers to a known cell death suppressing gene belonging to the Bcl-2 family or a gene homologous thereto. The gene homologous to the known cell death suppressing gene belonging to the Bcl-2 family is intended to refer to a gene encoding for a protein including at least one region selected from the group consisting of BH1, BH2 and BH3 regions, preferably a gene encoding for a protein including at least two regions selected from the group consisting of BH1, BH2 and BH3 regions, more preferably a gene encoding for a protein including BH1 and BH2 regions, and most preferably a gene encoding for a protein including all of the BH1, BH2 and BH3 regions.

Regions which are highly conserved may be easily searched and identified by aligning an amino acid sequence encoded by a gene of interest with an amino acid sequence of a known Bcl-2 family protein by using a commercially available computer analysis software (Gene Works, IntelliGenetics, Inc.).

The cell death suppressing activity of the obtained gene may be determined according to a method described in Miura et al., *Cell Technology*, vol. 14, No. 2:145–153, 1995. Specifically, a gene of interest is introduced into a Rat1 cell in which cell death is known to be induced by removing serum from a culture medium (Kumar, S. et al., *Genes Dev.* 8, 1613–1626, 1994). Serum is then removed from the medium. After 4 days, a rate of cell death of the recombinant Rat 1 cell is observed. In the case where the cell death is significantly suppressed in the recombinant Rat1 cell, the gene of interest is considered to have a cell death suppressing activity.

The cell death suppressing activity of the obtained gene may also be determined according to a method described in Eguchi et al., *Experimental Medicine*, vol. 13, No. 16, 24–31, 1995. Specifically, a gene of interest is introduced into a cell derived from a rat Pheochromocytoma strain PC12. About $10^5$ cells are convolved on a 6 cm dish and put into a chamber adapted for a low oxygen concentration. Then, the oxygen concentration in the chamber is decreased by using, for example, BBL GasPac Plus (Becton Dickinson). The number of surviving cells is quantitated over time using trypan blue, wherein the time is set to 0 at a point where the concentration of oxygen is reduced to 100 ppm. Since it is known that about half of the cells are killed when they are cultured under a low oxygen concentration of 100 ppm or lower (i.e., a condition under which apoptosis is induced) for 48 hours, the gene of interest is considered to have a cell death suppressing activity when a rate of the cell death is observed to be significantly suppressed.

The term "gene having a cell death suppressing activity" as used herein, therefore, refers to a gene which is confirmed to have a cell death suppressing activity according to at least one of the above-described methods or an equivalent thereof.

Procedures for producing a DNA library used for screening a gene homologous to a known cell death suppressing gene, stringent conditions for hybridization to a probe, and procedures for cloning a gene are well known to those skilled in the art. For example, see Maniatis et al., "Molecular Cloning", *A Laboratory Manual*, 2nd Ed., Cold Spring Harbor Laboratory Press, Cold Spring Harbor, N.Y., 1989.

The ced-9 gene may be screened by, first, isolating a total RNA from *C. elegans,* and then, obtaining a full-length cDNA for ced-9 by RT-PCR using the total RNA as a template. Preferably, 5'-TTGAATTCGAGATGACACGCTGCACGGCGG-3' (SEQ ID NO:1) may be used as a primer. Specifically, a first strand cDNA is synthesized from mRNA, which is then subjected to PCR using the primer of SEQ ID NO:1 and 5'-GGGAATTCGTTACTTCAAGCTGAACATCAT-3' (SEQ ID NO:2), thereby obtaining a cDNA of interest.

The bcl-xL gene may be isolated in a similar manner by using suitable primers.

PCR is performed in accordance with the manufacturer's instructions for the commercially available kits or instruments, or by a method well known to those skilled in the art.

The thus-obtained cell death suppressing gene derived from an animal or other origin may be introduced into a plant by being linked with a suitable plant expression vector. Alternatively, the cell death suppressing gene may be introduced into a plant by using a transformation method in which a nucleic acid is directly introduced in the plant (e.g., an electroporation method, a particle gun method, a calcium phosphate method or a polyethylene glycol (PEG) method).

The term "plant" as used herein includes monocotyledon and dicotyledon. Examples of particularly preferable plants include tobacco, green pepper, eggplant, melon, tomato, sweet potato, cabbage, spring onion, broccoli, carrot, cucumber, citrus fruit, Chinese cabbage, lettuce, peach, rice, potato, barley, wheat, and apple. Unless indicated otherwise, a "plant" as used herein includes any one of a plant body, a plant organ, a plant tissue, a plant cell and a seed. Examples of the plant organ include a root, a leaf, a stem, a flower and the like. Examples of the plant cell include callus and a suspension culture cell.

The term "plant expression vector" as used herein refers to a nucleic acid sequence in which various regulatoly elements, such as a promotor for regulating expression of a cell death suppressing gene, are linked to each other in such a manner as to be operative in a host plant cell. Preferably, the plant expression vector may include a plant promoter, a terminator, a drug resistant gene and an enhancer. It is well known to those skilled in the art that a type of the plant expression vector and a type of the regulator element may be varied depending upon the host cell. A plant expression vector used according to the present invention may further contain a T-DNA region. The T-DNA region enables the gene to introduce into plant genome via Agrobacterium mediated transformation.

The term "plant promoter" as used herein refers to a promoter expressed in a plant. Examples of plant promoters include, but are not limited to, promoters whose expressions are induced by a certain kind of stress, for example, a promoter of a gene encoding an infection specific protein PR-1a of tobacco (hereinafter, referred to as "tobacco PR-1a promoter"), or promoters which express consitutively, for example, a Cauliflower mosaic virus 35S promoter (hereinafter, referred to as "CaMV 35S promoter") and a promoter of nopaline synthase (Pnos).

The term "terminator" as used herein refers to a sequence positioned downstream of a region of a gene encoding a protein, which is involved in the termination of transcription of mRNA, and the addition of a poly A sequence. The terminator is known to contribute to the stability of mRNA, thereby affecting the expression level of a gene. Examples of the terminator include, but not limited to, a CaMV 35S terminator, a terminator of a nopaline syntase gene (Tnos), and a terminator of a tobacco PR-1a gene.

A drug resistant gene is desirable to allow a transgenic plant to be easily selected. As the drug resistant gene, a neomycin phosphotransferase II (NPTII) gene for conferring kanamycin resistance, a hygromycine phosphotransferase gene for conferring hygromycine resistance, and the like are preferably used.

Examples of promoters for expressing the drug resistant gene include, but not limited to, an E12Ω promotor, a tobacco PR-1a promoter, a CaMV 35S promotor, and a nopaline syntase promoter. Preferably, the E12Ω promotor is used which constitutively expresses a gene of interest at a high level. The E12Ω promoter includes two enhancer regions of the CaMV 35S promoter lined in tandem (En 35S: −417 to −90), the CaMV 35S core promoter and a Ω region of a tobacco mosaic virus (Gene 217: 217, 1987), the CaMV 35S promoter and the Ω region being positioned downstream of the tandem enhancer regions (see plasmid pST10 disclosed in Japanese Laid-Open Publication No. 7-250685). The E12Ω promoter has an activity which is 10 to 20 times greater than that of the CaMV 35-S promoter.

An enhancer may be used to enhance expression of a gene of interest. As the enhancer, an enhancer region containing a sequence upstream of the above-mentioned CaMV 35S promoter is preferable. A plurality of enhancers may be used per a gene of interest.

A vector used in the present invention for constructing a plant expression vector may preferably be a pBI-type vector, a pUC-type vector, or a pTRA-type vector.

The pBI-type and pTRA-type vectors may introduce a gene of interest, via Agrobacterium, into a plant. A pBI-type binary vector or a pTRA-type intermediate vector may be preferably used. Examples of the pBI-type vector include pBI121, pBI101, pBI101.2 and pBI101.3. These vectors contain a gene from a region (T-DNA region), which is introduced into a plant via Agrobacterium mediated transformation. These vectors also contain a NPTII gene (for providing kanamycin resistance) which is expressed under the control of a plant promoter to serve as a marker gene.

Use of the pUC-type vector may allow a gene to be directly introduced into a plant. Examples of the pUC-type vector include pUC18, pUC19 and pUC9.

The plant expression vector according to the present invention may be produced by using a recombinant DNA technique well known to those skilled in the art. Preferably, a cell death suppressing gene derived from an animal is introduced downstream of the promoter of the above-mentioned vector.

A plant expression vector may be introduced into a plant cell by using a method well known to those skilled in the art. For example, a method in which a plant expression vector is introduced via Agrobacterium or a method in which a plant expression vector is directly introduced into a cell are known. The method using Agrobacterium may be performed, for example, as described in Nagel et al., FEMS Microbiol. Lett., 67, 325, 1990. According to this method, Agrobacterium is first transformed with, for example, a plant expression vector by electroporation, and then the thus-transformed Agrobacterium is infected to a plant cell by a method described in S. B. Gelvin et al., Plant Molecular Biology Manual, Academic Press Publishers. Examples of a method for directly introducing a plant expression vector into a cell include an electroporation method and a gene gun method. These methods are well known in the art and a method suitable for the plant to be transformed may be suitably selected by those skilled in the art.

The cells in which plant expression vectors have been introduced are selected based on their drug resistance such as kanamycin resistance. Thereafter, the cells may be regenerated as a plant tissue, a plant organ or a plant body by using a conventional method. Furthermore, seeds may be obtained from the plant body.

By PCR analysis using a pair of primers, whether or not the cell death suppressing gene has been introduced into the transgenic plant may be determined. For example, when a gene of interest is introduced into a transgenic plant by a plant expression vector containing a terminator of nopaline syntase, PCR may be performed by using 5'-AGACCGGCAACAGGATTCAA-3' (SEQ ID NO:5), a sequence for terminator of a nopaline syntase, as a 3' primer. In the case where the gene of interest is the C. elegans ced-9 gene, a 5' primer may be 5'-CCTCTTCGTTTACACATCGC-3' (SEQ ID NO:3). In the case where the gene of interest is the human bcl-xL gene, a 5' primer may be 5'-ACAAGGAGATGCAGG-3' (SEQ ID NO:4). The resulting PCR product is subjected to agarose gel electrophoresis. Presence of the gene of interest in the transgenic plant is confirmed when a DNA having the same mobility as that of a positive control is amplified.

Expression of the introduced cell death suppressing gene may be confirmed by a method well known to those skilled in the art. For example, the expression may be confirmed in accordance with Northern blot analysis of total RNA extracted from a leaf of a plant using DNA corresponding to the introduced gene, that is, for example, cDNA of ced-9 or bcl-xL or a partial sequence thereof, as a probe.

In order to confirm expression of a cell death suppressing gene products derived from an animal or other origin in a plant, a method well known to those skilled in the art (e.g., Western Blotting) may be used. For example, expression may be confirmed as follows: A protein sample extracted from a transgenic plant is separated by SDS-polyacrylamide gel electrophoresis (hereinafter, simply referred to as "SDS-PAGE") as described in Leammli et al., Nature 227:680–685, 1970 and transferred to a suitable membrane. The membrane is incubated with an antibody against the protein of interest. The band of interest is immunochemically detected, thereby confirming expression of the gene product of interest. In order to detect expression of a human bcl-xL gene product, a protein sample extracted from a leaf is separated by SDS-PAGE and transferred to a membrane. The membrane is incubated with a polyclonal antibody against a human Bcl-xL protein. Then, for example, the membrane is incubated with alkaline phosphatase-conjugated anti-Rabbit IgG antibody. The reaction is visualized by hydrolysis of BCIP (5-bromo-4-chloro-3-indolyl-phosphate) and NBT (Nitroblue tetrazolium) as a substrate, thereby detecting the expression of the gene product.

The stress resistance of a transgenic plant may be detected as resistance to treatment with UV irradiation, resistance to treatment with a herbicide which generates superoxide (e.g., 1,1-dimethyl-4,4-bipyridinium dichloride; sold under a trademark "paraquat") and/or resistance to a salt stress.

Typically, a UV irradiation treatment may be performed by using UV-B light. The UV-B irradiation treatment may be performed by using a Toshiba UV-B lamp (Toshiba FK-208E). Two sets of two UV lamps, each UV lamp horizontally located 20 cm away from each other, are prepared. The wavelengths of the UV light radiated from the UV-B lamps are mostly UV-B (290–320 nm), the rest being UV-C (260–280 nm) and UV-A (340–360 nm). Wavelengths less than 290 nm can be blocked by a cellulose diacetate filter. A distance between the UV-B lamp and the top of plant may be adjusted such that an amount of the UV-B irradiation is suitable. The UV-B radiation is supplemented with white light at an intensity of 100 $\mu mol^{-2}S^{-1}$ (16 hours of irradiation per day). Thus, measurements for UV-B light intensity are always performed in the presence of white light. The irradiation intensity may be measured with a Spectroline digital radiometer (Spectronic Corporation, Westbury, N.Y.) and may be calibrated based on NIST standard.

An example of a herbicide which generates superoxide includes paraquat (Trademark). The herbicide treatment is performed by immersing a leaf disk in a herbicide solution under continuous light.

In the case of the UV-B treatment, a transgenic plant is found to have obtained UV-B resistant if indicative phenomena are suppressed in the transgenic plant compared with those of a non-transgenic plant. Such phenomena include abnormal gloss of the surface of the leaf irradiated with UV, wilting of the leaf irradiated with UV, and withering. In addition, the transgenic plant is found to have obtained UV-B resistance or herbicide resistance if discoloration of the leaf of the transgenic plant after the UV-B irradiation treatment or the herbicide treatment is suppressed compared with that of the non-transgenic plant.

Alternatively, chlorophyll content may be measured for examining effect of the UV-B irradiation treatment or the herbicide treatment. Specifically, after a predetermined period of the above-described treatment, chlorophyll is immediately extracted from the leaf using N,N-dimethylformamide. The extract is then measured by a spectrophotometer. The chlorophyll content of a transgenic plant and a non-transgenic plant are measured. The transgenic plant is found to have obtained resistance if the chlorophyll content of the transgenic plant is greater than that of the non-transgenic plant.

A high salt concentration as stated herein refers to a concentration of salt at which growth of a control plant is inhibited. The term "salt stress" refers to a condition where a plant is grown in an environment of such high salt concentration. A range of the high salt concentration is well known to those skilled in the art. For example, resistance to a solution with 0.1 M or 0.2 M NaCl concentration may be an indicator of salt resistance.

The resistance to salt stress may be examined as follows. A transgenic plant and a control plant are exposed to an environment of high salt concentration, for example, by immersion in and allowing the plant to absorb salt water. Seedlings or plants grown to a height of 30 to 40 cm may be used as plant samples. Changes in the weight and changes in morphology (e.g., a degree of etiolation or chlorosis, and a degree of formation of a abscission layer) are compared between the transgenic plant and the control plant. The transgenic plant is found to have obtained resistance to salt stress if the change in the weight (typically, decrease in the weight) and the observable changes in morphology of the transgenic plant are suppressed after the exposure to the salt environment compared to those of the control plant.

As can be appreciated by those skilled in the art, the stress resistance of a transgenic plant may alternatively be detected under conditions other than but equivalent to the above-described conditions.

According to the present invention, the term "stress resistant plant" refers to a transgenic plant which is conferred at least one of: resistance to UV irradiation treatment; resistance to a herbicide treatment, which generates superoxide; and resistance to salt stress treatment.

Hereinafter, the present invention will be described by way of illustrative examples. A restriction enzyme, a plasmid, and the like used in the following examples are available from commercial sources.

EXAMPLE 1
Preparation of a Plant Expression Vector

A binary vector pBE2113 shown in FIG. 1 was used as a starting material of a plant expression vector. As described in Japanese Laid-Open Publication No. 7-250685, the plant expression vector is produced by using the binary vector pBI121 (produced by Clontech), which contains drug resistant gene regions (Pnos, NPTII and Tnos) as a starting material, and in which a promoter region sequence for E12Ω is introduced.

EXAMPLE 2
Isolation of a Cell Death Suppressing Gene Derived from an Animal and Construction of a Plant Expression Vector Total RNA was isolated from *C. elegans* by using a TRIsol (Life Technologies, Inc.). A first strand cDNA was synthesized from mRNA. Then, a full-length cDNA for ced-9 was synthesized by RT-PCR using 5'-TTGAATTCGAGATGACACGCTGCACGGCGG-3' (SEQ ID NO:1) as a primer. Then, PCR was performed using Pfu polymerase (produced by Stratagene), while using SEQ ID NO: 1 as a 5' primer and 5'-GGGAATTCGTTACTTCAAGCTGAACATCAT-3' (SEQ ID NO:2) as a 3' primer. DNA was denatured at 94° C. for 1.5 minutes, annealed at 55° C. for 2.5 minutes and subjected to extension reaction at 72° C. for 2 minutes. This cycle was repeated 25 times. The PCR product was cloned into EcoRI site of pBluescript, thereby obtaining a plasmid pM61.

Figure 2:
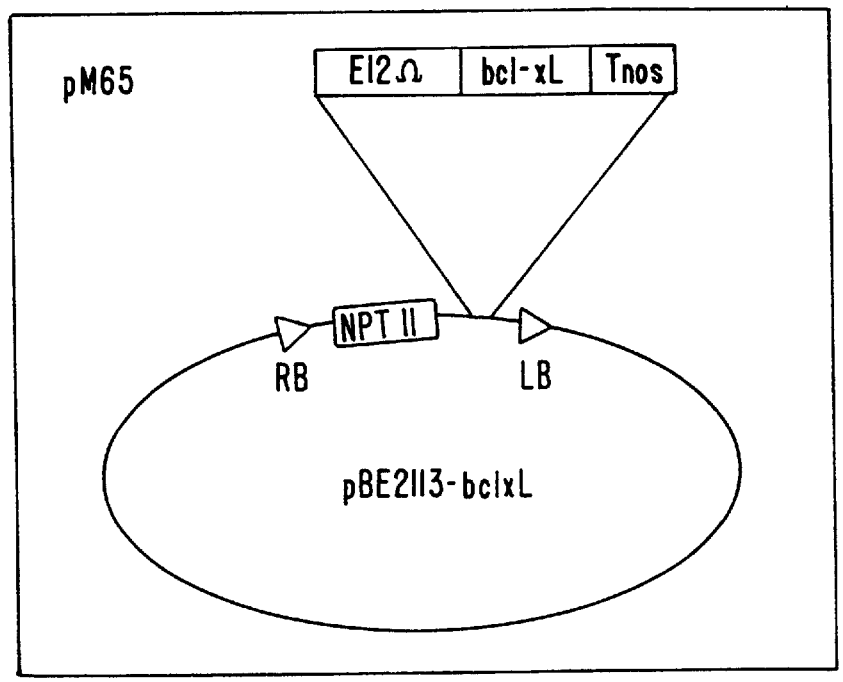
FIG. 2 is schematic diagrams showing the plasmid (pM65) containing a gene for human bcl-xL and a plasmid (pM66) containing a gene for C. elegans ced-9.
Figure 2:
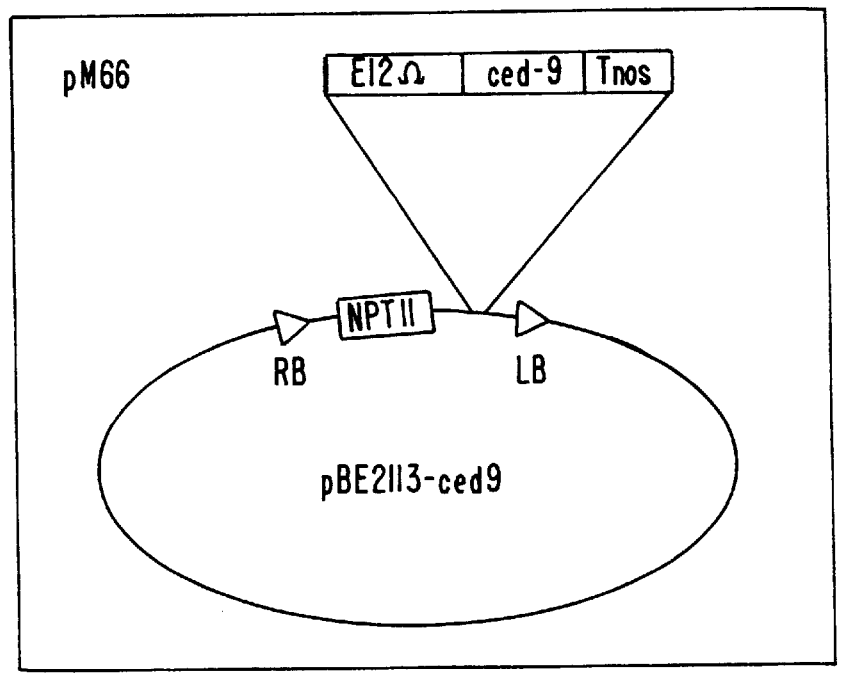

On the other hand, a human bcl-xL gene was isolated from a human cDNA library (produced by Clontech) by PCR using 5'-ATGTCTCAGAGCAACCGGGAGCTGGTGGTT-3' (SEQ ID NO:6) as a 5' primer and 5'-TCATTTCCGACTGAAGAGTGAGCCCAGCAG-3' (SEQ ID NO:7) as a 3' primer. The conditions of the PCR are the same as those described above. The isolated full-length human bcl-xL cDNA was cloned into EcoRI site of pBluescript, thereby obtaining a plasmid pM21. The SalI site of pM21, or HindIII site of pM61 were changed to BglII by using a synthetic linker. The resulting plasmids are named pM21-BgI and pM61-BgI, respectively. A BglII-SacI fragment of pM21-Bgl or a BglII-SacI fragment of pM61-Bgl was isolated and cloned downstream of E12Ω of pBE2113. A vector having a human bcl-xL gene was named pM65 and a vector having a *C. elegans* ced-9 gene was named pM66. The expression vectors pM65 and pM66 are schematically shown in FIG. 2.

EXAMPLE 3
Introduction of an Expression Vector in Tobacco Plant
(Transformation of *Agrobacterium tumefaciens*)

*Agrobacterium tumefaciens* was cultured at 28° C. in a culture medium containing 250 μg/ml of streptomycin and 50 μg/ml of rifampicin. A cell suspension culture was prepared, and the expression vector (pM65 or pM66) was introduced into the above-mentioned bacterium by electroporation in accordance with a method described in Navel et al., *Microbiol. Lett.*, 67, 325, 1990.

Transformations were performed in the same manner, for one case, by using a plasmid (pBI121:35S-GUS) containing a GUS (glucuronidase) gene linked to a CaMV-35S promoter and, for the other case, by using a plasmid (35S-POX) containing a POX (peroxidase from rice) gene (Ito et al., *Plant Cell Reports*, 13:361–366, 1994) fused with the CaMV 35S promotor in order to compare transformation efficiency.
(Transformation of Tobacco)

Agrobacteria transformed with the plasmid pM65 or pM66 according to the above method was obtained and subjected to suspension culture in a YEB medium (*DNA cloning*, vol. 2, p. 78). The culture medium was then 20-fold diluted with sterilized water and then cocultivated with leaf disks of tobacco (Nicotiana tabacum cv. Samsun NN). After a few days, the bacteria was removed on a culture medium containing anti biotic. The leaf disks were subcultured on a selection medium every two weeks. The transgenic tobacco cells were selected and regenerated by a conventional method. As a result, 20 independent kanamycin resistant transformants in which the human bcl-xL gene (pM65) was introduced, and 29 independent kanamycin resistant transformants in which C.elegance ced-9 gene (pM66) was introduced. Furthermore, 20 independent kanamycin resistant transformants were obtained in the case of plasmid 35S-GUS and 47 independent kanamycin resistant transformants were obtained in the case of plasmid 35S-POX. The results are shown in Table 1.

TABLE 1

|  | Number of independent kanamycin resistant transformants | Number of independent transformants having gene of interest | Percentage (%) |
|---|---|---|---|
| M65 transformant (E12Ω-bcl-xL) | 20 | 20 | 100 |
| M66 transformant (E12Ω-ced-9) | 29 | 28 | 97 |
| Control transformant (35S-Gus) | 20 | 14 | 70 |
| Control transformant (35S-POX) | 47 | 34 | 73 |

Introduced gene is shown in parentheses

The transformants in which a cell death suppressing gene was introduced had a gene of interest (bcl-xL or ced-9) at a very high percentage (97% or higher). These results were also confirmed by the later-described PCR. On the other hand, the transformants in which the cell death suppressing gene was not introduced had a gene of interest (GUS or POX) at only about 70%. These facts indicate that cells in which the cell death suppressing gene was introduced are advantageous in surviving.

EXAMPLE 4
Confirmation of Transformation by a PCR Method

Figure 3:
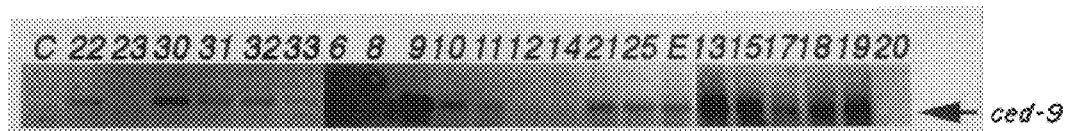
FIG. 3 is an electrophoresis photograph showing the result of RT-PCR for confirming the expression of an introduced gene in a transgenic plant (M66), where C denotes control plant and each number denotes an individual number of the transgenic plant.

Total RNA was extracted from a transgenic tobacco in which the C.elegance ced-9 gene (pM66) was introduced by a conventional method, and cDNA was synthesized. Then, RT-PCR was performed by using 5'-CCTCTTCGTTTACACATCGC-3' (SEQ ID NO:3) as a 5' primer and 5'-AGACCGGCAACAGGATTCAA-3' (SEQ ID NO:5), a sequence for nopaline syntase terminator as a 3' primer. The PCR conditions were the same as those in Example 2. The resulting PCR product was subjected to electrophoresis on an agarose gel to determine whether or not a DNA fragment having the same mobility as that of the control was amplified. The results are shown in FIG. 3. The presence of the introduced gene in the transformants was confirmed.

Figure 4:
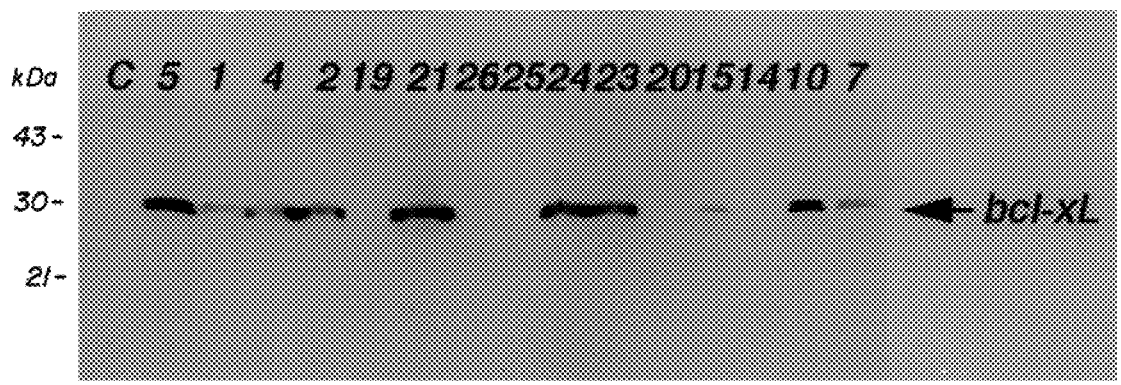
FIG. 4 shows the result of Western blot analysis using an anti-Bcl-xL antibody for confirming expression of a human bcl-xL gene product in a transgenic plant (M65) in which a cell death suppressing gene from an animal is introduced, where C denotes control plant and each number denotes an individual number of the transgenic plant.

EXAMPLE 5
Detection of Expression of a Cell Death Suppressing Gene Product in a Transgenic Plant Expression of a human bcl-xL gene product was confirmed by Western Blotting. Four leaf disks with a diameter of about 7 mm obtained from each of a transgenic tobacco Samsun NN in which human bcl-xL gene (pM65) was introduced and a wild type Samsun NN were ground in 20 µl of 125 mM Tris-HCl, pH 6.8 (containing 0.1% SDS, 20% glycerol, 28 mM 2-mercaptoethanol, 10 µg/ml bromophenol blue), centrifuged at 16,000 rpm for 10 minutes and boiled for 5 min, whereby supernatant was collected as a protein fraction. The protein fraction was subjected to a 12.5% SDS-PAGE, and transferred to an Immobilion-P membrane (produced by Milipore). Thereafter, the membrane was incubated with the rabbit polyclonal antibody (produced by MBL) against the human bcl-xL protein. The membrane was washed and incubated with alkaline phosphatase-conjugated anti-Rabbit IgG antibody (at a dilution 1:1000, produced by KPL Laboratory). The band of interest was visualized by hydrolysis of BCIP and NBT as a substrate. The results are shown in FIG. 4. Expression of the human Bcl-xL protein in the transgenic plant was confirmed.

EXAMPLE 6
Detection of RNA in a Transgenic Plant by Northern Blotting

Figure 5:
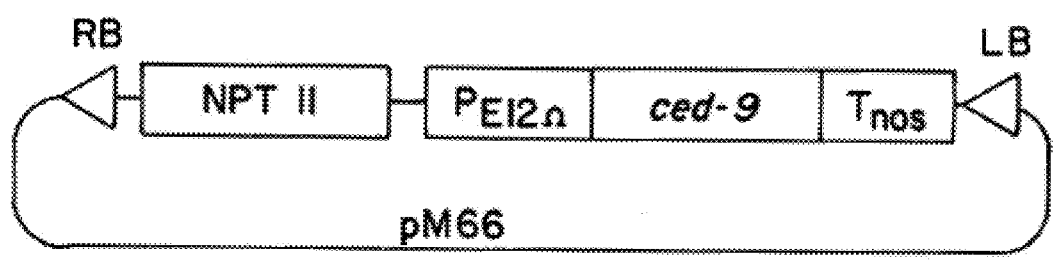
FIG. 5 is an aoutoradiogram showing the result of Northern blot analysis for confirming expression of a C. elegans ced-9 gene in a transgenic plant (M66), where C denotes control plant and each number denotes an individual number of the transgenic plant, also shown is a schematic diagram showing expression vector of pM66.
Figure 5:
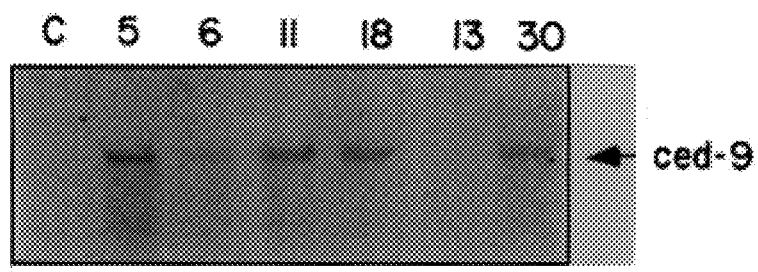

Expression of a ced-9 gene in a transgenic plant was confirmed by Northern blotting. According to a conventional method, a total RNA extracted from a regenerated tobacco leaf was subjected to electrophoresis on an agarose formaldehyde gel, and blotted on a Hybond-N membrane (produced by Amersham). The mRNA of interest was detected by using DNA corresponding to the introduced gene, for example, cDNA for ced-9 or bcl-xL as a probe. The results are shown in FIG. 5. Expression of the introduced gene was confirmed in the transgenic plant.

EXAMPLE 7
Acquisition of UV Resistance in a Transgenic Plant

According to a method described in Example 6, a M65-21 plant in which a human bcl-xL gene was introduced and a M66-30 plant in which a C. elegans ced-9 gene was introduced are selected among transgenic tobacco plants in which expression of a cell death suppressing gene was confirmed. These plants were examined for UV resistance. The UV irradiation treatment was performed under the above-described conditions by using a Toshiba UV-B lamp.

First, the wild type tobacco plants were irradited with UV-B through a filter and UV-B without a filter. The tobacco directly irradiated with UV light (260–360 nm) was found to have a higher sensitivity against UV light than that irradiated via the filter (290–360 nm). Accordingly, it was considered that UV-C emphasizes adverse effect of the UV-B.

Figure 6A:
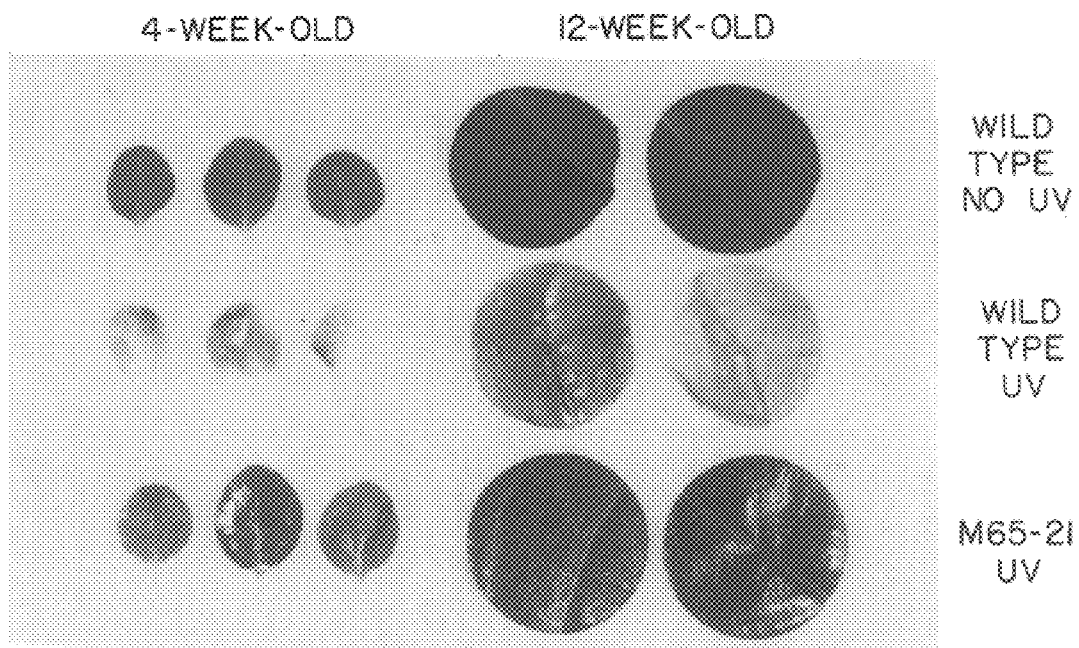
FIG. 6A is a photograph showing 4-week-old leaves after a UV irradiation treatment and leaf disks obtained from 12-week-old leaves after the UV irradiation treatment.
Figure 6B:
FIG. 6B is a photograph showing plantlets obtained after 10 days of UV-B irradiation treatment.

A 4-week-old leaf, a 12-week-old leaf disk, and a plantlet of self-pollinated plants of the second generation of each of M65-21 (bcl-xL), M66-30 (ced-9) and a wild type tobacco plant were irradiated with UV-B without the filter. The transgenic tobacco and a wild type tobacco (control) plants were exposed to UV-B (25 kJ/m$^2$) for 10 days. No visual change was observed at 4 and 5 days after the treatment. The wild type wilted at Day 7 or 8 after the treatment and eventually withered. The transgenic M65-21 (bcl-xL) and M66-30 (ced-9) plants did not show changes or were slightly morphologically disrupted. The results are shown in FIG. 6. FIG. 6A is a photograph showing the 4-week-old leaves and the leaf disks from 12-week-old leaves, which were treated with UV-B irradiation for 10 days. FIG. 6B is a photograph showing the plantlet irradiated with UV-B light for 10 days. These results indicate that the transgenic plants have obtained resistance to UV-B light and thus presumably exhibit resistance to UV irradiation under natural environment.

EXAMPLE 8
Inhibiting Effect on Chlorophyll Degradation in a Transgenic Plant

Figure 7:
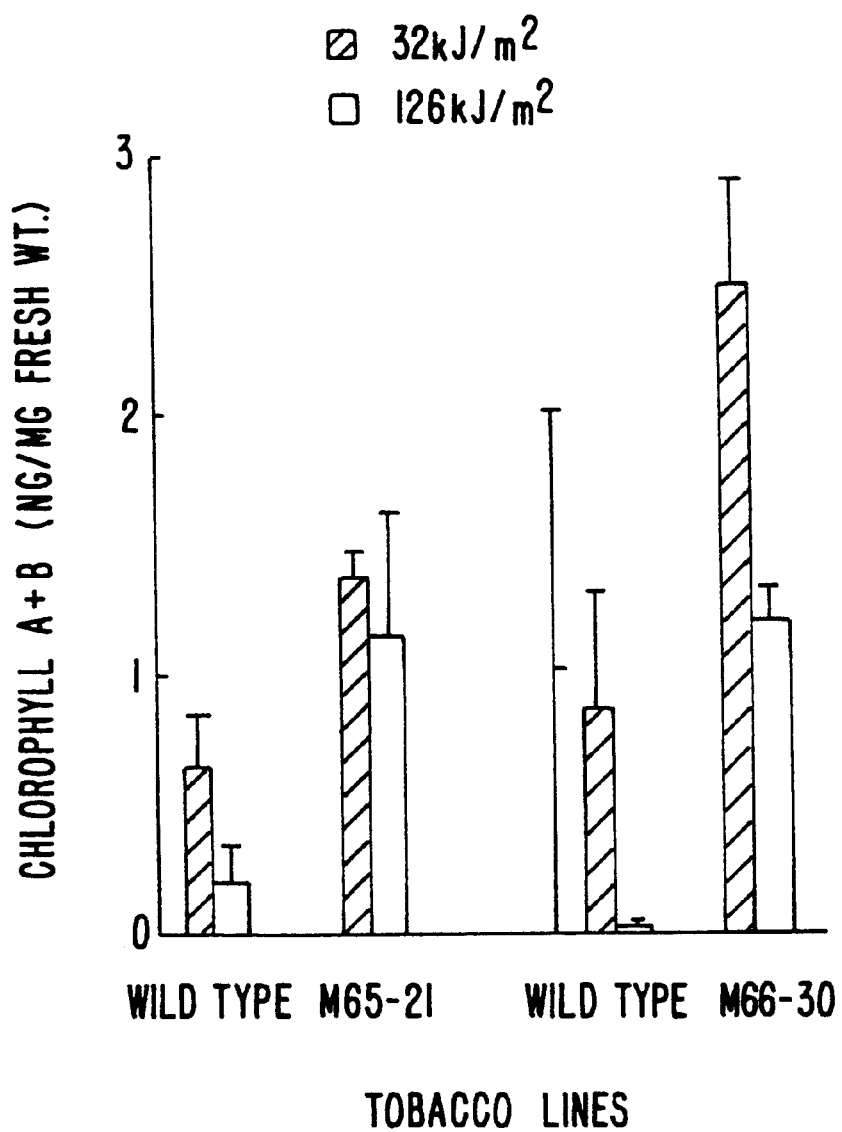
FIG. 7 is a graph showing that chlorophyll content of a plant in which a cell death suppressing gene from an animal is introduced, is only slightly reduced even after the UV irradiation treatment.

In the same manner as in Example 7, by using a UV-B without a filter, leaf disks from 12-week-old leaves of the M65-21 (bcl-xL) plant, the M66-30 (ced-9) plant and a wild type tobacco plant were exposed to UV-B light (32 kJ/m$^2$) for 10 days. After the UV-B irradiation treatment, chlorophyll was extracted from the treated leaf disks by using N,N-dimethylformamide, and measured according to a method of Borra et al., *Biochemica et Biophysica Acta*, 975:384–394, 1989. Specifically, chlorophyll a was measured by using a formula: 13. 43×(an absorbance at a wavelength of 663.8 nm)−3.47×(an absorbance at a wavelength of 646.8 nm), and chlorophyll b was measured by using a formula: 22.9×(an absorbance at a wavelength of 646.8 nm)−5.38×(an absorbance at a wavelength of 663.8 nm), thereby obtaining a chlorophyll content a+b. In addition, a treatment was also performed under the condition of UV-B irradiation at 126 kJ/m$^2$. In this case, since the leaf disks began to etiolate on Day 3, the treatment was performed for 2 days. The results are shown in FIG. 7. In all of the treatments, chlorophyll remained undegraded for the transgenic M65-21 (bcl-xL) and M66-30 (ced-9) plants.

EXAMPLE 9
Resistance to Paraquat (Trademark) in a Transgenic Plant

Figure 8:
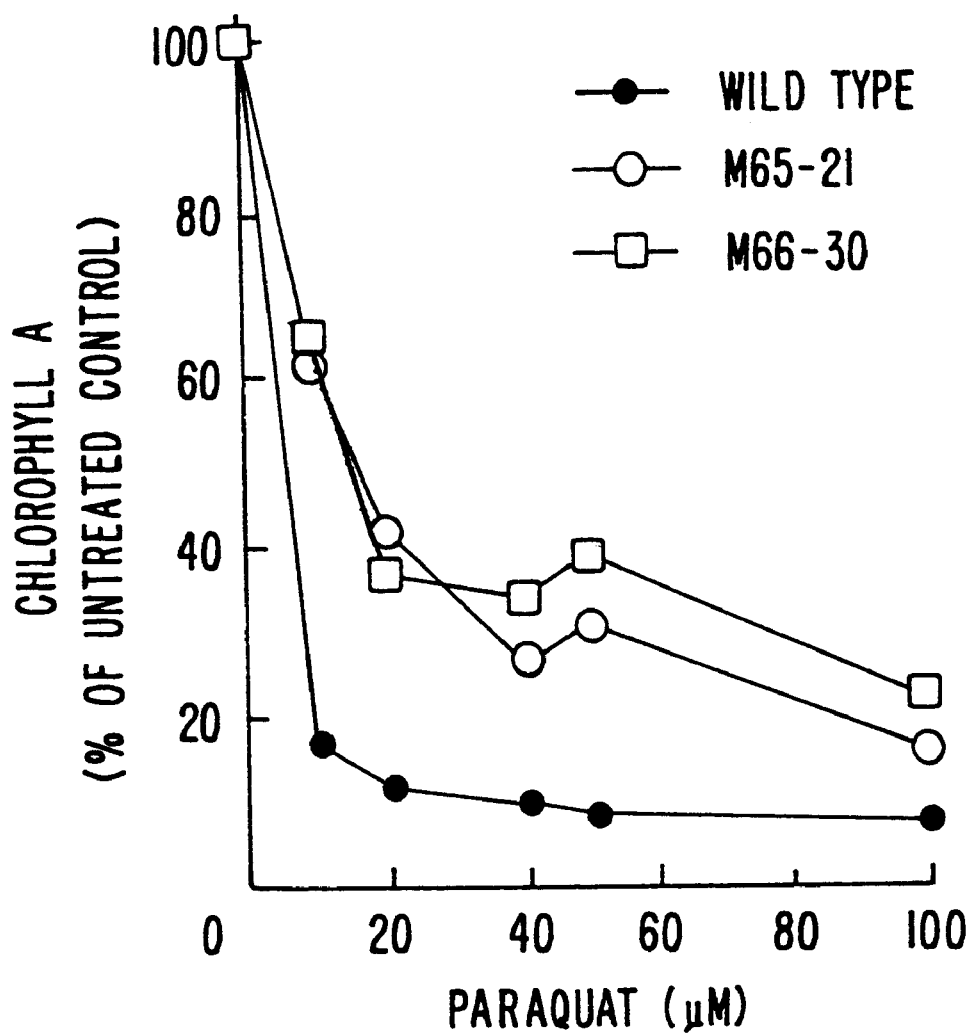
FIG. 8 is a graph showing that a plant in which a cell death suppressing gene from an animal is introduced has obtained paraquat resistance.

Paraquat is a herbicide which generates superoxide and free radicals in a chloroplast. Since the transgenic M65-21 (bcl-xL) and M66-30 (ced-9) plants exhibited resistance to chlorophyll degradation, both of them were considered to have resistance to paraquat as well. Tobacco leaf disks were immersed in a 0 to 100 µM paraquat solution under continuous light. In the same manner as in Example 8, chlorophyll was extracted and measured for the concentration of chlorophyll. The results are shown in FIG. 8. The transgenic M65-21 (bcl-xL) and M66-30 (ced-9) tobacco plants both exhibited resistance to paraquat.

EXAMPLE 10
Acquisition of Salt Resistance in a Transgenic Plant

Salt resistance was evaluated by selecting the M65-21 plant in which human bcl-xL gene is introduced and the M66-30 plant in which *C. elegans* ced-9 gene is introduced among transgenic plants in which expression of a cell death suppressing gene was confirmed.

(A) A seed of an self-pollinated plant of the second generation of M65-21 (hereinafter, referred to as "M65-21-2"), a seed of self-pollinated plants of the second generation of M65-30 (hereinafter, referred to as "M65-30-3") and a seed of 35S-GUS as a control were each seeded on an agar medium containing 50 µg/ml of kanamycin. After 2 months, seedlings were carefully taken out from the agar medium and agar on the roots were removed by washing. Then, each seedling was put into a 2 ml Eppendolf tube (where the lid is cut off) containing 2.2 ml of water, 0.1 M NaCl solution or 0. 20 M NaCl solution such that the roots thereof were immersed in the solutions. The tubes were supported by a tube stand and put into a transparent acrylic box. Then, resistance of the plants to salt was evaluated under the conditions where light irradiation and a temperature are at 3000 lux (16 hours/day) and 25° C., respectively.

In addition, as a control plant, a non-transgenic tobacco (wild type tobacco) plant was seeded on an agar medium which did not contain kanamycin.

Figure 9:
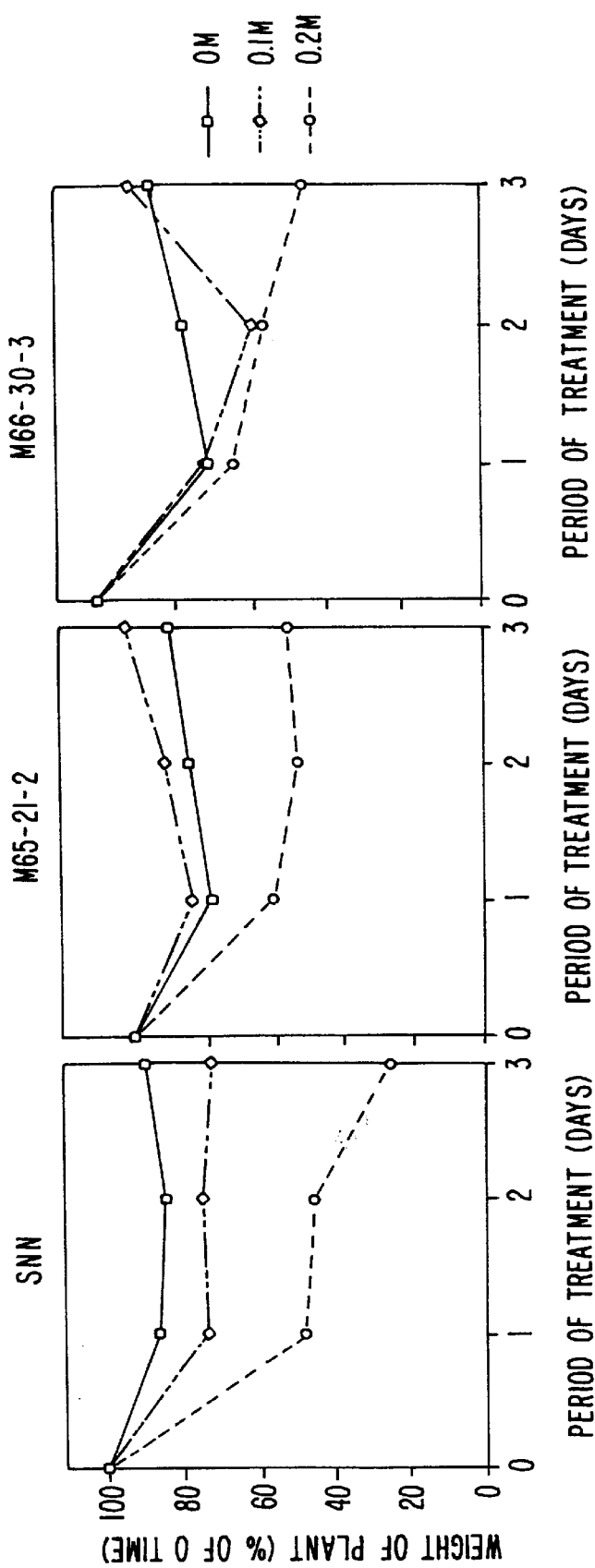
FIG. 9 is graphs showing changes in weights of plants in which a cell death suppressing gene from an animal is introduced (M65-21 and M66-30 plants) and a wild type tobacco plant, under a stress of salt.

(1) The weight of each seedling was measured over time, and the resistance of each plant to salt was evaluated quantitatively. The results are shown in FIG. 9. Values shown in the graphs are average values of 5 seedlings of each plant.

For seedlings immersed in water (i.e., 0 M NaCl), the weights thereof decreased 1 day after the transplantation. This was considered due to the fact that the seedlings had to be taken out in the air from closed petri dishes and placed in the tube media. Thereafter, the weights of the seedlings immersed in water gradually increased.

In the case of the wild type tobacco plant, decrease in the weight of the seedling treated with 0.1 M NaCl was significant, and the weight of the seedling treated with 0.2 M NaCl was more decreased.

On the other hand, in the case of the transgenic plants 65-21-2 (bcl-xL) plant and M66-30-3 (ced-9) plant, decrease in the weights of the seedlings treated with 0.1 M NaCl were substantially undetectable. Even for the seedlings treated with 0.2 M NaCl, the decrease in the weights thereof was suppressed compared to the wild type tobacco plant.

Figure 10:
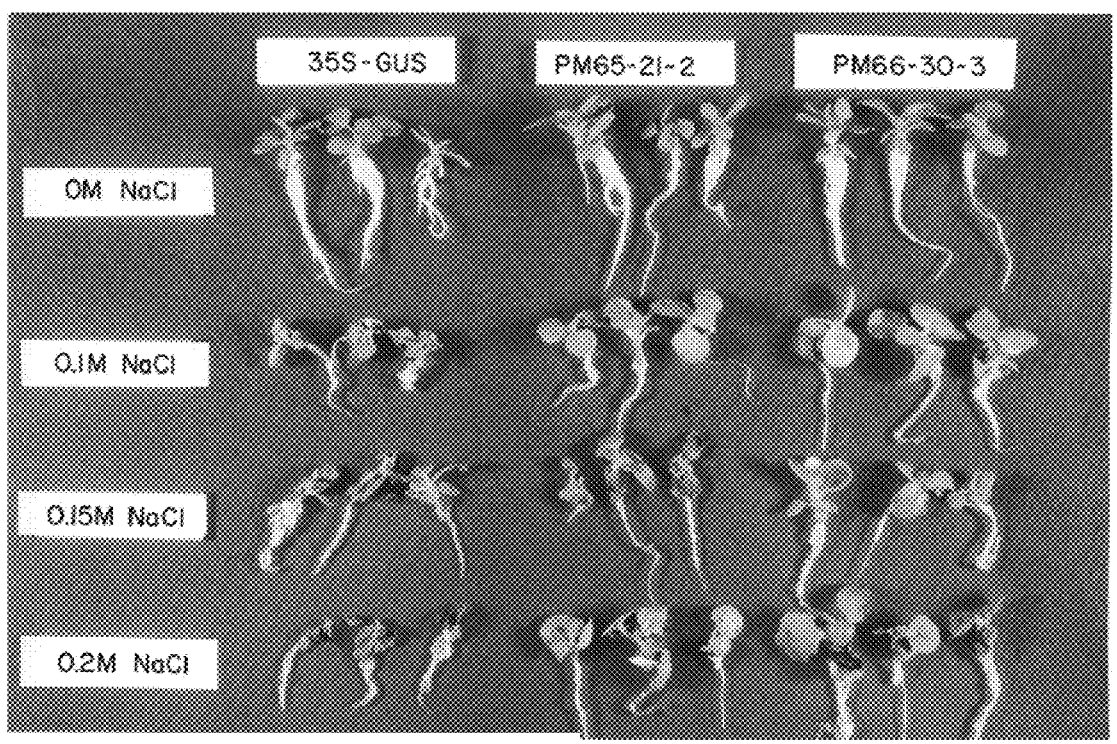
FIG. 10 is a photograph showing seedlings of plants in which a cell death suppressing gene from an animal is introduced (M65-21 and M66-30 plants), and seedlings of a 35S-GUS plant. These plants were left for 3 days under various salt concentrations.

(2) For the 35S-GUS plant (control) treated under the exactly same conditions as above, the same results as those obtained for the wild type tobacco plants were obtained. A photograph was taken 3 days after the treatment (FIG. 10). The 35S-GUS plant was entirely disrupted under a high concentration of salt, where the leaves were wilted and the growth of the roots was inhibited. Whereas, the transgenic tobacco plants were less disrupted compared to the control plant.

Figure 11:
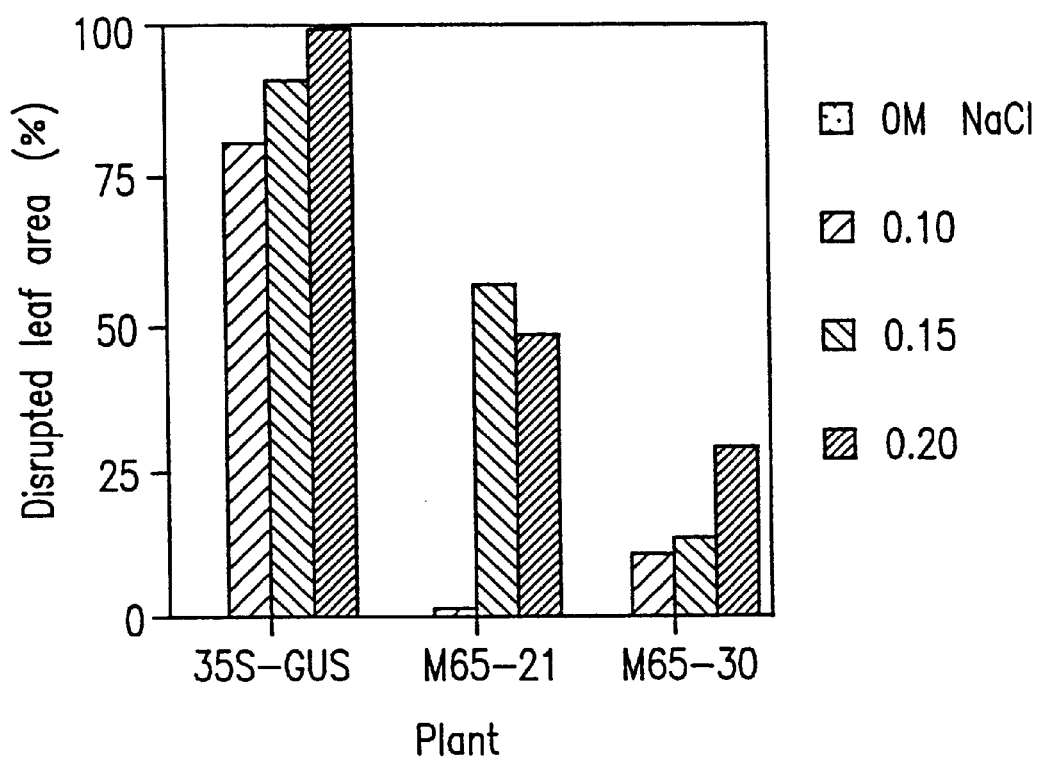
FIG. 11 is a graph showing disrupted leaf areas of plants in which a cell death suppressing gene from an animal is introduced (M65-21 and M66-30 plants) and that of a 35S-GUS plant (control).

(3) Areas of the disrupted leaves by the above-described treatment were observed with a stereoscopic microscope. FIG. 11 is a graph showing the percentages of the disrupted areas of the leaves. The results represent the fact that the above-described transgenic plants are conferred higher resistance to salt than those of the control plants, including that the M65-21 plant was hardly affected by 0.1 M NaCl.

(4) Same types of seedlings as those used in the above-described experiments (1) through (3) (i.e., seedlings obtained 2 months after seeding) were newly prepared. These seedlings were transplanted on two agar media which did not contain kanamycin. 3 days after the transplantation, a NaCl aqueous solution was added to one medium so that a final NaCl concentration of the medium was 0.2 M (NaCl treated medium), and the same amount of water was added to the other medium (control medium).

Figure 12:
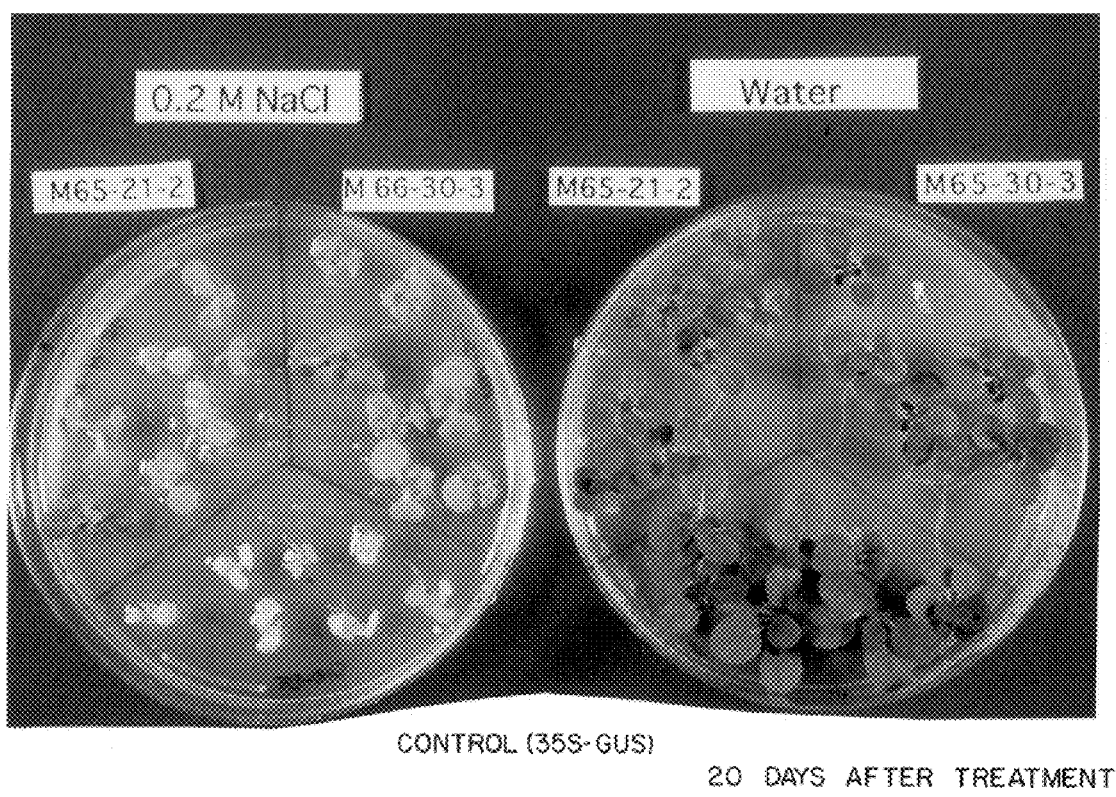
FIG. 12 is a photograph showing salt resistance (0.2 M NaCl) of plants in which a cell death suppressing gene from an animal is introduced (M65-21 and M66-30 plants) and that of a 35S-GUS plant, and, as controls the same types of plants absorbing water instead of salt are shown. The plants in which the cell death suppressing gene is introduced have obtained salt resistance.

Growth of the plants on both media were observed. 20 days after the transplantation, the 35-GUS plant and the transgenic plants in the control medium grew favorably and produced green leaves (FIG. 12, right). On the other hand, growth of the plants in the NaCl treated medium was inhibited on the whole (FIG. 12, left).

However, in the NaCl treated medium, the transgenic tobacco plants were less disrupted by the salt compared to the control 35S-GUS plant. All of the leaves of the control plant were etiolated and had indication of chlorosis. On the other hand, the transgenic plants had resistance to 20 days of salt treatment and many of their leaves maintained green color.

(B) Salt resistance was further evaluated by a method in which stems of 30 to 40 cm tobacco plants which were grown in vermiculite were cut and immersed in a NaCl solution and absorbed thereof. In addition, $Na^+$ and $Cl^-$ concentrations in lower leaves of the plants were quantitated so as to analyze the mechanism of resistance of the plant to salt stress.

Figure 13:
FIG. 13 is a photograph showing a wild type plant (control) and plants in which a cell death suppressing gene from an animal is introduced (M65-21 and M66-30 plants), after being left for 9 days in an 0.2 M NaCl condition. The plants were cut off at the stem and put into the solution of 0.2 M NaCl. The plants in which the cell death suppressing gene is introduced have obtained salt resistance.

Stems of potted wild type tobacco plant and transgenic M65-21-2 and M66-30-3 tobacco plants were cut below the plant body (about 7 cm above the root). Each of the plants were put into a 500 ml erlenmeyer flask containing 300 ml 0.2 M NaCl solution or 300 ml water (control) such that the cutoff stems were immersed in the solutions, thereby being maintained under the conditions of 25° C. and 3000 lux (16 hours/day) for 9 days. After 9 days, etiolation of the wild type tobacco plant was evident. The lower leaves of the wild type plant macerated and thus were likely to form abscission layers which led to loss of leaves. On the other hand, the transgenic M65-21-2 and M66-30-3 plants clearly had healthier appearance and the formation of abscission layers of the lower leaves did not progress (FIG. 13).

Lower leaves of the above-described plants were harvested. Whole leaves including petioles of leaves were ground together with distilled water, and centrifuged at 10,000×g for 15 minutes. Ion conductivity, and $Na^+$ and $Cl^-$ contents of the resulting supernatant were measured.

Electric conductivity was measured using an electric conductivity detector (Shimatsu CDD-6A). A supernatant of 100 μl was injected into the detector. Displayed measurement value μS/cm was divided by a cell constant (25), thereby obtaining an electric conductivity S (siemens).

The $Na^+$ concentration was quantitated by a CS12A column using a DIONEX ion chromatograph DX-100 and Cl-concentration was quantitated by a DIONEX AS4A column using a DIONEX ion chromatograph 2000i.

Results of the analysis of the ion conductivities are shown in Table 2. All of the lower leaves of the plants absorbing 0.2 M NaCl contained electrolyte at higher concentration than those of the plants absorbing water instead of NaCl (control). Particularly, electrolyte contents of two wild type tobacco plants, SNNa and SNNb, increased by 146% and 113%, respectively, compared to the control plant SNN absorbing water instead of NaCl. The electrolyte contents contained in the lower leaves of the transgenic tobacco plants were obviously less than that of the wild type SNN tobacco, and the increase compared to an original plant was 37% to 78% at most. Accordingly, the transgenic tobacco plants are considered to either excrete once absorbed NaCl from certain leaf tissues by some mechanism, or absorbe a smaller amount of NaCl.

In addition, $Na^+$ and $Cl^-$ concentration were measured. As a result, in the control tobacco SNN, increase in the $Na^+$ concentration accumulated in the lower leaves was 6 to 8 times greater than that of the plant absorbing water. On the other hand, in the transgenic tobacco plants, increase in a $Na^+$ concentration was greatly suppressed. Particularly in the case of M66 plant, the increase of the $Na^+$ concentration was only 2 to 3 times greater than that of the plant absorbing water (Table 2). Similar results were obtained for $Cl^-$ concentrations (data not shown).

TABLE 2

| Plant | Protein (mg/gFW) | Na (ppm) Total amount | Na (ppm) Increased amount with respect to the control | Conductivity (uS) Total amount | Conductivity (uS) Increased amount with respect to the control |
|---|---|---|---|---|---|
| SNN (−NaCl) | 7.6 | 0.76 | — | 926 | — |
| SNNa (+NaCl) | 13.4 | 6.55 | 5.79 (× 7.6) | 2,274 | 1,348 (146%) |
| SNNb (+NaCl) | 16.2 | 5.48 | 4.72 (× 6.2) | 1,974 | 1,048 (113%) |
| M65-21a (+NaCl) | 15.8 | 4.33 | 3.57 (× 4.7) | 1,266 | 340 (37%) |
| M65-21b (+NaCl) | 13.4 | 4.34 | 3.58 (× 4.7) | 1,545 | 619 (67%) |
| M66-30a (+NaCl) | 10.4 | 2.39 | 1.63 (× 2.1) | 1,373 | 447 (48%) |
| M66-30b (+NaCl) | 14.6 | 3.38 | 2.62 (× 3.4) | 1,648 | 722 (78%) |

These results suggest that these plants in which the cell death suppressing gene products from animals are overexpressed exhibit resistance to salt by preventing excessive accumulation of $Na^+$ and $Cl^-$.

Figure 14:
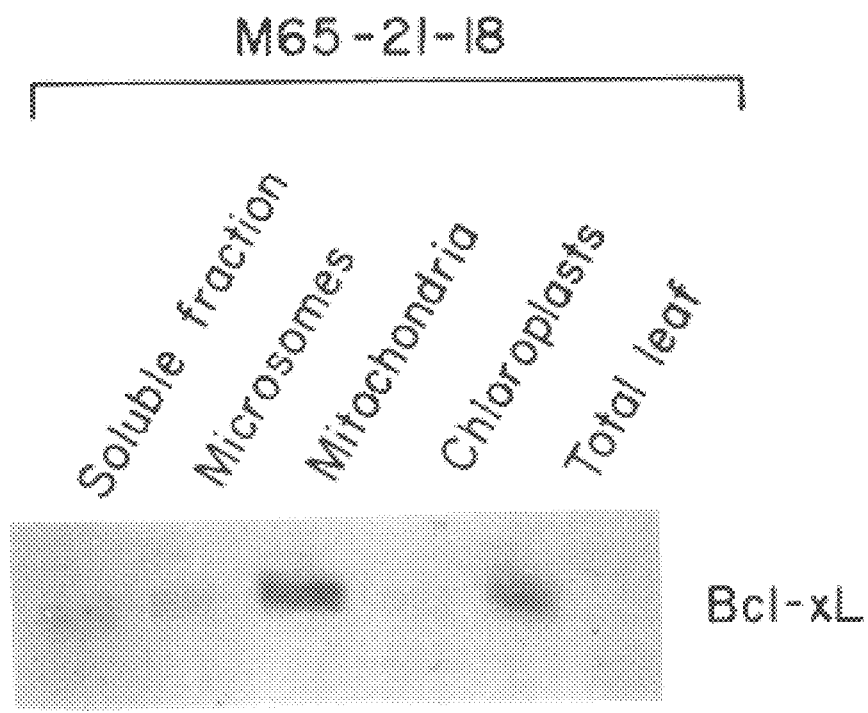
FIG. 14 is an electrophoresis photograph showing a result of a Western blot analysis for confirming localization of Bcl-xL protein in a cell of a transgenic plant. It is shown that the Bcl-xL protein is localized in the mitochondria fraction.

(6) In order to further analyze the salt resistance mechanism, an intracellular organella of a leaf of a M65-21 plant was fractionated by a diffrential centrifugation, and the localization of Bcl-xL protein was examined. The results obtained by Western blot analysis are shown in FIG. 14.

From these results, it was found in a protein level that majority of the Bcl-xL protein was localized in a mitochondrial fraction.

In an animal, it is considered that these cell death suppressing gene products are present in a mitochondrial membrane, thereby preventing disfunction of mitochondria to suppress cell death. The results obtained from the above-described examples according to the present invention show that a cell death suppressing protein from an animal equally functions in a plant and that not only UV resistance and paraquat resistance may be provided but also salt resistance may be provided. Protection against disfunction of an intracellular organella (e.g., mitochondria) which is caused by stress is considered responsible for this mechanism.

A plant introduced with a cell death suppressing gene may exhibit resistance to UV irradiation, resistance to a herbicide which generates superoxide and resistance to salt stress. According to the present invention, a plant which is conferred resistance to various stresses is provided. The plant is advantageous in agriculture and in plant breeding. Furthermore, according to the present invention, a method for providing a plant which is conferred resistance to stresses is provided.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A stress resistant plant in which a cell death suppressing polynucleotide is introduced, wherein the cell death suppressing polynucleotide belongs to the Bcl-2 family and encodes for a peptide having a cell death suppressing activity.

2. A stress resistant plant according to claim 1, wherein the cell death suppressing polynucleotide is a *Caenorhabditis elegans* ced-9 polynucleotide.

3. A stress resistant plant according to claim 1, wherein the cell death suppressing polynucleotide is a human bcl-xL polynucleotide.

4. A stress resistant plant according to claim 1, wherein the stress is a stress caused by UV irradiation.

5. A stress resistant plant according to claim 1, wherein the stress is a oxidative stress caused by a herbicide which generates superoxide.

6. A stress resistant plant according to claim 1, wherein the stress is a stress caused by salt.

7. A method for producing a stress resistant plant, comprising the steps of:

introducing a cell death suppressing polynucleotide into a plant cell, wherein the cell death suppressing polynucleotide belongs to the Bcl-2 family and encodes for a peptide having a cell death suppressing activity; and regenerating the plant cell in which the cell death suppressing polynucleotide is introduced to a plant body.

8. A method according to claim 7, wherein the cell death suppressing polynucleotide is incorporated into a plant expression vector.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

TTGAATTCGA GATGACACGC TGCACGGCGG                                      30

(2) INFORMATION FOR SEQ ID NO:2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:2:

GGGAATTCGT TACTTCAAGC TGAACATCAT                                      30

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:3:

CCTCTTCGTT TACACATCGC                                                 20

(2) INFORMATION FOR SEQ ID NO:4:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

ACAAGGAGAT GCAGG                                                      15

(2) INFORMATION FOR SEQ ID NO:5:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

-continued

AGACCGGCAA CAGGATTCAA                                           20

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATGTCTCAGA GCAACCGGGA GCTGGTGGTT                                 30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCATTTCCGA CTGAAGAGTG AGCCCAGCAG                                 30